United States Patent [19]

Minin et al.

[11] Patent Number: 5,512,573
[45] Date of Patent: Apr. 30, 1996

[54] USE OF PHTHALOYLHYDRAZIDE DERIVATIVES AS ANTI-HYPOXIC AND DEFENSIVE AGENTS

[75] Inventors: Leonid Minin; Slava Saizev, both of Geneva, Switzerland

[73] Assignee: L.I.M.A.D. Limited, Douglas, Isle of Man

[21] Appl. No.: 198,896

[22] Filed: Feb. 18, 1994

[30] Foreign Application Priority Data

Feb. 19, 1993 [CH] Switzerland .................. 531/93

[51] Int. Cl.[6] .................. A61K 31/50; C07D 237/32
[52] U.S. Cl. .................. 514/248; 514/863; 544/237
[58] Field of Search .................. 544/237; 514/248, 514/863

[56] References Cited

U.S. PATENT DOCUMENTS

| | | | |
|---|---|---|---|
| 2,420,702 | 5/1947 | Drewitt | 260/569 |
| 3,007,937 | 11/1961 | Rogers | 260/309.5 |
| 3,644,361 | 2/1972 | Bellascio | 260/250 |
| 3,870,792 | 3/1975 | Inoue et al. | 424/250 |

FOREIGN PATENT DOCUMENTS

| | | |
|---|---|---|
| 1182224 | 6/1956 | France . |
| 2490074 | 4/1982 | France . |
| 8200624 | 1/1982 | WIPO . |

OTHER PUBLICATIONS

CA 117: 83219m 1992 Wong, Res. Commun, Chem. pathol. Pharmacol. 1992 76(1), 3–32.

*Primary Examiner*—Gary Geist
*Assistant Examiner*—Catherine Kilby Scalzo
*Attorney, Agent, or Firm*—Notaro & Michalos

[57] ABSTRACT

The invention concerns the use of phthaloylhydrazide derivatives and their salts as anti-hypoxic and defensive agents, with special focus on the use of 5-aminophthaloyl-hydrazide and its salts, when administered in high doses.

4 Claims, No Drawings

USE OF PHTHALOYLHYDRAZIDE DERIVATIVES AS ANTI-HYPOXIC AND DEFENSIVE AGENTS

FIELD AND BACKGROUND OF THE INVENTION

This invention concerns the use of phthaloylhydrazide* derivatives with as general formula

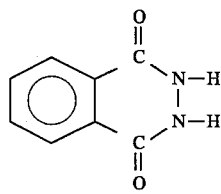

which, surprisingly, have been shown to possess thus far unknown anti-hypoxic and defensive properties in living animal organisms.

Translator's note: The Italian term 5-aminoftalidrazide has consistently been translated as 5-aminophthaloylhydrazide, although "aminophthalylhdrazide" is, according to chemists who were consulted, an acceptable alternative. A generic name for this particular compound (Merck Index) is "Luminol".

These properties include the possibility of triggering a pronounced anti-hypoxic and defensive action when administered to the organism in doses of 10 to 300 mg/kg.

Attempts have been made to use 2,3 dihydrophthalazine -1,4 dione and some of its derivatives to decrease serum cholesterol levels (Hall J. M., et al.: Effect of 2,3 dihydrophthalazine-1,4 dione on Sprague-Dawley rats lipid metabolism and serum lipoproteins. Biomed Biochem Acta V.47 (4–5) pp. 423–433; 1988) by modifying levels of lipids with very low density. However, due to certain signs of toxicity, the use of the drug in this context has been limited.

SUMMARY OF THE INVENTION

The anti-toxic and defensive action of the derivatives of this group of compounds were not known and have not been described in the literature.

We succeeded for the first time in discovering a new and entirely unique action mechanism of phthaloylhydrazides which manifested itself only with the use of large doses in vivo.

This unique action mechanism discovered by us is not obvious from analyses of the chemical properties.

We have demonstrated in experiments that the phthaloylhydrazide derivatives which have different radicals replacing the hydrogen atoms of the benzene ring or the lateral groups, e.g., 2,3 dihydrophthalazine-1,4 dione; 5-amino-2,3-dihydrophthalazine- 1,2 dione; sodium salt of 5-amino-2, 3-dihydrophthalazine- 1,2 dione; 4,5-amino-2,3- dihydrophthalazine- 1,2 dione; and 4-methyl-4,5-diamino-2,3 dihydrophthalazine-1,2 dione possess a pronounced pharmacological activity and, if they are administered in the doses indicated above, also provide an anti-hypoxic and defensive action eliminating the effects of excessive leukocyte activity.

Both compounds, i.e., 4-aminophthaloylhydrazide and 5-aminophthaloylhydrazide, have shown that they possess major therapeutic effects. However, 5-aminophthaloylhydrazide and its salts met the prerequisites in successive (pharmacological and toxicological) tests and was therefore chosen as a basic drug suitable for use in medicine.

DESCRIPTION OF THE PREFERRED EMBODIMENTS

Chemical Data a) Physical properties 5-aminophthaloylhydrazide belongs to the pyridazine group with low molecular weight (less than 200). Its melting point is less than 250° C.
Profile of pH solubility: pH of 6.5, c= 2 mM
pH of 7.4, c= 12 mM
The octanol/water distribution coefficient is pH-dependent. For pH 7.4, c= 0.2 b) Chemical properties
pK= 6.3
Stability: The compound is stable in anhydrous conditions (can be preserved for over one year). It is sometimes unstable in aqueous solutions (probably due to cooxidation with certain mixtures of substances which are present in trace quantities in the concentrations). The expiration period for the aqueous solution exceeds 10 to 20 hours.
Active rotation: absent.

Toxicological Data a) Acute toxicity

Acute toxicity tests were performed on two animal species (mice, rats). More than 80 mice and 100 rats were used. The pharmaceutical was administered orally and intraperitoneally in doses of 500 and 2500 mg/kg (individual doses). The period of observation was 14 days. No morphological alteration was observed of the tissues of the liver, kidneys, heart and brain. The percentage of lethal outcome in the test group did not exceed that of the control group.

b) Mutagenicity

Mutagenicity was measured by means of Ames' bacterial testing method. The tests were performed with strains of *S. typhi* TA 100, TA 102, and TA 97. The microsome activator method was used whereby rat liver was induced with methylcolanthrene. The data show that 5-aminophthaloylhydrazide does not posses inhibitory or mutagenic activity in concentrations between 0.01 and 2 mg/ml.

c) Reproduction toxicity

Teratogenic tests and embryotoxicity tests were performed on 58 female pregnant rats. A single dose was injected intraperitoneally on days 1, 3, 7, 10, 14 and 17 of gestation (60 mg/kg). The rats were decapitated on day 21 of the pregnancy and the uteruses and fetuses were examined. No abnormality of the fetuses was observed. The site of uterine attachment, the number, weight and mortality of the fetuses did not differ from those obtained for the control group.

d) Cytotoxicity

The cells used as subject matter included lymphocytes, macrophages and fibroblasts. Viability following a 24-hour in vitro exposure with 5-aminophthaloylhydrazide in concentrations of 0.01 to 0.8 mmols/liter was determined by means of protein incorporation and/or synthesis. No toxicity was observed for any of the dosage levels tested.

The allergenic activity of the drug was examined in guinea pigs. No signs of allergy were observed when the drug was administered either subcutaneously or orally. No erythema was observed at the site of administration, even in the event of large doses. In the case in which doses of 20 to 100 mg were administered, there were no symptoms of local irritation.

Study of the Effect on the Central Nervous System

To study the pharmacological properties on the central nervous system, doses of 40 to 80 mg per kilogram of body weight were used. The choice of doses was based on safety criteria governing the use of medicines.

The neuropharmacological effects were studied in male mice of undefined strain which had reached sexual maturity. The mice, weighing 18 to 20 g, were given a solution of the drug intraabdominally. The neuropharmacological effects were studied on the basis of changes in the natural orientation reflex, in induced aggressiveness, and in muscle tone. The change in the natural sense of orientation was recorded according to the current method. To study the effect of the drug on induced aggressiveness, the electrical stimulation method (pain caused by electric current) was used.

The change in muscle tone was measured by means of the "pivot pin" method.

In doses of 40 to 80 mg per kilogram of body weight, the drug did not suppress the natural orientation reflex, nor did it cause changes in muscle tone or modifications in the pain threshold.

The effect of the drug on the length of Hexenalum-induced anesthesia was studied, i.e., the drug was administered in doses of 10 to 30 mg per kilogram of body weight, 15 minutes before the administration of the Hexenalum solution in a dose of 80 mg/kg. With the doses studied, 5-aminophthaloylhydrazide did not cause a noteworthy extension of the Hexenalum-induced sleep.

The study of the anticonvulsive activity of the drug established that preventive administration of the drug to mice in doses of 40 and 80 mg per kilogram of body weight did not prevent Corazolum- and strychnine-induced convulsions following intravenous titration of convulsive drugs. In the doses indicated above, 5-aminophthaloylhydrazide did not reduce the induced convulsions.

Research on the Effects of the Sodium Salt of 5-aminophthaloylhydrazide on the Cardiovascular System.

The effect of the sodium salt of 5-aminophthaloylhydrazide on blood pressure (BP) was examined in male rats weighing 230 to 270 g, in a controlled experiment where the rats were anesthetized with urethane. The blood pressure was recorded on tape by means of an electrical kymograph.

At the same time, we recorded the electrocardiogram in the second standard position as well as any changes in frequency and depth of respiration by means of a Morey capsule. We administered 5-aminophthaloylhydrazide in the femoral vein in the form of an aqueous solution prepared in a 2% sodium bicarbonate solution (pH= 8.2), in doses of 40 mg/kg, 80 mg/kg and 50 mg/kg. Research on 5-aminophthaloylhydrazide was performed on 16 rats.

Results:

The intravenous administration of the 1% solution of 5-aminophthaloylhydrazide at the rate of 0.6 ml/minute was followed by a brief rise in blood pressure, i.e., 1.57±5.93% on the average, compared to the initial level. No sudden fluctuations in the increase in blood pressure were observed during the administration of 5-aminophthaloylhydrazide, either in the dose of 40 mg, or in the dose of 50 mg per kilogram of body weight. Five minutes after the start of the administration of aminophthaloylhydrazide, the pressure began dropping gradually to return to the initial level within an average of 30 minutes.

Thirty minutes after the administration of 5-aminophthaloylhydrazide, fluctuations in the level of blood pressure were on the average 2.79±0.72 compared to blood pressure levels at the beginning.

In the course of the experiment, no changes were observed in the electrocardiogram parameters of the heart, and no impairment of the respiratory functions was observed in those cases in which 5-aminophthaloylhydrazide was administered in doses of 20 mg and 50 mg per kilogram of body weight.

Accordingly, the experimental study of the 5aminophthaloylhydrazide administered in doses of 40 and 50 mg per kilogram of body weight did not present any evidence of a negative effect on the cardiovascular system or the respiration. The tendency observed, i.e., the rise in blood pressure immediately after the intravenous administration, may be explained as a (compensatory) reaction of the cardiovascular system of the rats in response to a change in alkaline blood levels; this factor was demonstrated by the administration of a 2% sodium bicarbonate solution.

Forms of Supply:

The forms of supply most frequently used were: vials for intravenous and intramuscular injection, suppositories for rectal administration, and solutions for gargling.

1) The sodium salt of 5-aminophthaloylhydrazide was adapted for intramuscular and intravenous administration.

The sodium salt of 5-aminophthaloylhydrazide, with a purity level of no less than 96 to 98%, was diluted with the smallest possible volume of specially deionized water, and was poured in vials with opaque walls, so that each vial contained 100 mg of the drug. Subsequently, we lyophilized the vials, closed them with sterile caps, sealed the caps and sterilized the vials by maintaining them at a temperature of 140° to 160° C. for 60 minutes.

The containers used for the animals contained a large quantity of the drug, i.e., 250 mg.

The aqueous solutions of the drug remain fully active for 60 to 80 minutes.

The high therapeutic effectiveness of the drug is determined by the following properties:

1) The antioxidant action in vivo, stabilized on the basis of the change in the ethane and pentane contents of the air inhaled by the animals subjected to the experiment.

2) The drop in the adhesion capacity of the leukocytes.

The latter factor is rather important because it is known that in case of acute hypoxia (myocardial infarct, attack, etc.), extensive stretches of tissue will suffer lesions due to the activity of the leukocytes. In fact, the leukocytes will penetrate the ischemic hearth when the blood circulation resumes.

The leukocyte attack is at the basis of the rejection reaction in organ and tissue transplantation.

Finally, the formation of an excess of free oxygen radicals in affected tissue in patients suffering from psoriasis will determine to a large extent the increase in clinical symptoms of the disease.

When administered intravenously in the form of sodium salt in doses of 100 to 200 mg/kg, the release period of the drug is 65 to 75 minutes. In any event, the effects which manifest themselves (change in adhesion properties of the leukocytes), take place in the course of 6 to 11 hours.

The length of the anti-hypoxic effect is determined by the administered dose of the drug. However, even if the dose is increased beyond 100 mg/kg, the effect does not basically increase. In the event of administration in doses of 60 to 80 mg, the anti-hypoxic activity of the action of the sodium salt of 5aminophthaloylhydrazide exceeds that of antioxidants used thus far in medical practice (Dibunolo, histidine, Organeia, etc.). To preserve the action, the drug must be administered every 12 hours.

These properties of the drug may be successfully used in reanimation where the number of effective drugs is limited.

Because of the number of lethal cases, myocardial infarct occupies a prominent place among acute diseases. The peak of mortality is reached on the third through sixth day from the onset of the disease, when the circulation in the myocardium resumes.

The antioxidants, which are analogous to the proposed drug, do not provide the therapeutic effect under consideration because when the leukocytes enter the affected ischemic tissue, they not only release the radicals of the oxygen which damage the tissue, but also toxic enzymes and proteins.

The sodium salt of 5-aminophthaloylhydrazide administered one time intravenously in doses of 150 to 250 mg/kg, eliminates after 6 hours 75% of the leukocytes previously penetrated, and thus guarantees the survival of the affected tissue. At the same time, the leukocyte levels in the blood of the animals subjected to the experiments increased 2.5 times.

Also at the same time, the chance of survival of the treated animals increased. In the experimental group (to which the drug was administered), the percentage of surviving animals reached 80% ($p < 0.01$), while in the control group consisting of animals treated with antioxidants: the percentage was only 50% ($p > 0.05$).

Thus, there are no drugs at the present time which compare to the proposed drug with regard to therapeutic effectiveness and action mechanism.

Intramuscular injections of 5-aminophthaloylhydrazide proved less effective—the number of surviving animals grew (60%) but at a unreliable rate ($p > 0.05$).

Similar results were also obtained for a model of an ischemic attack. In a series of cases it was possible to prevent the effects of acute focal hypoxia through the administration of the drug. However, in this context, a single administration of the drug proved insufficient and the main therapeutic effect was obtained after two administrations of the drug at 12-hour intervals. The morphological research confirmed the results obtained.

The medical branch which has accelerated in recent years, i.e., organ and tissue transplantation, cannot develop fully because of the lack of therapeutic means to prevent a leukocytic attack on the transplant.

(Analogous) drugs used to that effect, i.e., hormones, immuno-depressants, etc., involve many complications and side effects, and are not sufficiently effective, even in combination.

A comparison of the analyses has shown that, as far as effectiveness is concerned, the proposed drug— in doses of 100 to 200 mg per kilogram of body weight—exceeds the hormonal drugs with long-term action known thus far (corticosteroids).

Treatment started on the second day following a skin transplant from another animal and continued for 45 to 50 days.

The combined administration of the salt of 5-aminophthaloylhydrazide, hormones and immuno-depressants, made it possible to increase the number of outside transplantations taking root in up to 40% of the cases. In another case, it was possible to obtain a noticeable extension of the period before rejection.

At present, corticosteroids and antimycotics, e.g., cyclosporine, are used for the treatment of psoriasis.

However, in most cases even a combined treatment has proved ineffective.

A daily administration to patients in doses of 12 to 20 mg/kg has changed the clinical picture of the disease.

A positive dynamic has been demonstrated, i.e, the itching disappeared, the temperature went down and the surface area of the affected zone shrunk.

The therapeutic effect of the preparation increased noticeably whenever the patches of skin were also treated with a 4% solution of 5-aminophthaloylhydrazide in a 10% solution of DMSO. In that case, all pathological signs could be eliminated in a short period of time, i.e., 10 to 12 days. At the same time, epithelization of the pustules occurred.

Histological analyses (biopsy samples) of residual pathological formations determined a decrease (by 80 to 92%) of the neutrophil contents in the altered epidermal cells.

These visual symptoms of the disease disappeared between days 45 and 55 following the start of the treatment. A recurrence was observed 4 to 8 months later. It is therefore appropriate to give the patients a preventive treatment for 10 to 15 days once every four months, with a drug dose of 10 to 15 mg/kg without topical treatment of the skin tissue.

The action of the drug used in the known doses has been confirmed in many cases.

In all cases, evidence was found of its high therapeutic efficacy and the advantages it offers compared to similar drugs known at this time.

The pharmacological studies conducted have shown the absence of toxicity in those cases in which the drug was administered to animal organisms.

EXAMPLE 1

We assessed the pharmacological activity on the basis of the resistance of the animals to hypoxia. For that purpose, we placed the animals (mice weighing 18 to 20 g) in an atmospheric pressure room and we "brought" them to an altitude of 10,400 meters at the speed of 100 meters per second. We administered the drug intravenously in doses of 10 to 300 mg, in 0.1 ml of physiological solution. In some cases, because of poor solubility, we injected the derivatives in the form of suspensions. The control animals received 0.1 ml of physiological solution.

Proof was provided that the main effect of the various drugs was evident in doses of 10 to 200 mg/kg.

Phthaloylhydrazide: 10 to 15 mg/kg 5-aminophthaloylhydrazide: 60 to 80 mg/kg 5-aminophthaloylhydrazide sodium salt: 50 to 70 mg/kg 4-aminophthaloylhydrazide: 105 to 130 mg/kg 4,5-aminophthaloylhydrazide: 150 to 180 mg/kg 4,5-methylaminophthaloylhydrazide: 160 to 200 mg/kg The degree of therapeutic effect was not the same either, and the life span of the animals subjected to the experiment fluctuated between limits of 88 and 299 seconds, while for the control animals it fluctuated and was $41 \pm 2.5$.

The greatest pharmacological activity was provided by the sodium salt of 5-aminophthaloylhydrazide in doses of 60 to 80 mg/kg, $222 \pm 45$; the smallest pharmacological activity by dimethyldiaminophthaloylhydrazide, i.e., $89 \pm 12$.

Conclusions: the phthaloylhydrazides possess a pronounced anti-hypoxic effect.

EXAMPLE 2

Experiments to test the resistance of the animals to high-level hypoxia were performed on 120 male mice weighing 18 to 20 g, and having reached sexual maturity.

Five minutes before the experiment, the animals were given the following doses intramuscularly:

the first group (control group), 0.1 ml of physiological solution;

the second group (test group), a 20% oil solution in a dose of 30 mg/kg;

the third group, 5-aminophthaloylhydrazide in a dose of 30 mg/kg;

the fourth group, 5-aminophthaloylhydrazide in a dose of 60 mg/kg;

the fifth group, 5-aminophthaloylhydrazide in a dose of 80 mg/kg;

the sixth group, 5-aminophthaloylhydrazide in a dose of 150 mg/kg;

the seventh group, the drug in a dose of 200 mg/kg.

The period of tolerance to hypoxia was determined by raising the animals to an altitude of 10,400 meters at the speed of 100 meters per second.

As can be derived form the data in the table, the drug extended life under conditions of high-level hypoxia in all cases. If in the dose of 30 mg per kilogram of body weight, the drug proved less therapeutically effective than the known antioxidant Dibunolo, the effectiveness of the drug exceeded that of Dibunolo in a reliable manner ($p < 0.001$) when the administered amount was increased to 100 mg.

The greatest therapeutic effect was recorded with the administration of the 80 mg/kg dose.

The last increase in the administered amount of the drug did not increase the therapeutic effect achieved.

EXAMPLE 3

Experiments were performed on 60 previously prepared rats. Thirty days before the start of the main experiment, a part of the coronary artery was tied off.

Next, after having supplied light anesthesia, we created by means of the obstruction of the vessel a massive hearth of myocardial ischemia. After 12 to 15 minutes, we suddenly restored the blood circulation.

We administered the sodium salt intravenously in doses of 30, 100, 200 and 250 mg per kilogram of body weight, immediately after having released the tie. In the control group, the rats were administered a physiological solution, while the test group was given the antioxidant Dibunolo (20% oily solution in a dose of 30 mg/kg).

The following observations were made:

1) In the series of control experiments, the animal mortality reached 60%. The lethal cases peaked on the second day. 2) In the test group, there was a tendency toward rising survival rates of the animals, but the results obtained were not reliable ($p > 0.05$).

3) The dose of 30 mg/kg did not prevent the death of the animals either ($p > 0.05$), although in the test group there were clear signs of a therapeutic effect.

4) The increase in the dose of the drug to 100 mg/kg and beyond led to an increase in the number of surviving animals ($p < 0.01$–$0.001$).

The percentage of surviving animals fluctuated for the various series between 80 and 100% and did not, in essence, depend on the ultimate increase in the drug dose. The ultimate increase in the drug dose was determined by technical difficulties.

The morphological analysis of the myocardium showed the presence of extensive necrotic hearths in the control series. In the test group, the damaged area could not be perceived visually. The tiny necrotic hearths were few and diffused.

We may therefore conclude that the greatest therapeutic effect occurred in the case of the intravenous administration of the drug in doses of 100 mg up to 300 mg per kilogram of weight.

EXAMPLE 4

We performed experiments on 50 mice of the pyramid by tying the carotid under light anesthesia. After 7 minutes, we released the tie and restored the blood circulation in the ischemic area. The mortality of the animals in the control group reached 50% and was not entirely prevented by the action of Dibunolo, histidine or other oxidants.

The drug administered in doses of 30 mg per kilogram of body weight did not affect the pathological process in a reliable manner. The percentage of surviving animals did not increase ($p > 0.05$).

A pronounced therapeutic effect was obtained in the case of intravenous administration of the drug in a dose of 100 mg/kg. In this group, 9 out of 10 animals survived.

In 8 cases, there were no symptoms of neurological impairment.

In the case of intramuscular administration of the same dose, the therapeutic effect was irrelevant. Six out of 10 animals survived, while symptoms of neurological impairment were recorded in 3 cases. However, it was determined that the intramuscular administration of the drug was not effective.

The ultimate increase in the amount of the drug did not lead to a reliable increase in the survival rate of the animals compared to the dose of 100 mg/kg. When a dose of 150 mg/kg was administered, the number of surviving animals reached 80%, but in 2 cases there were symptoms of damage to the central nervous system.

Two administrations of the drug with a 12-hour interval in doses of 100 mg/kg guaranteed the survival of 9 animals without symptoms of neurological impairment.

It should be pointed out that in the series of control experiments symptoms of neurological impairment were recorded in at least half of the surviving animals.

We can therefore state that in doses of 100 mg/kg, administered twice, the drug may be used with positive outcome for treatment of the most diffuse and severe disorders of the nervous system, acute alterations in the blood stream in the brain.

EXAMPLE 5

The experiments involved 30 chinchillas from which a strip of skin was removed measuring 2×2 cm. The resulting lesion was covered by an outside transplant. The animals were divided into three groups.

The first group was treated with traditional therapy (prednisolone and cyclosporine); the second group was given 5aminophthaloylhydrazide daily in a dose of 150 mg/kg; the third group received a combined treatment.

To assess the efficacy of the drug, the period before the rejection was measured and morphological studies were conducted.

As expected, the traditional treatment yielded the least pronounced therapeutic action. The rejection of the transplant occurred between day 31 and day 42. In the second series of experiments, this period increased in a reliable manner to 56 to 70 days, while in the third group the symptoms of transplant rejection occurred after 120 to 180 days. In four cases, there were no changes for one year (the observation did not extend beyond that time). During the morphological examination, no signs of transplant rejection were observed.

Conclusions:

When administered intravenously, 5-aminophthaloylhydrazide slowed the rejection process down considerably ($p < 0.01$) compared to traditional therapy. When combined with known measures, it even succeeded in a number of cases in preventing the rejection entirely.

EXAMPLE 6

Patient K., female, 35 years old, ill for 5 years. Was cured in the hospital several times during that period. Complained about itching, general weakness, unpleasant sensations in parts of the skin. Examination revealed that the skin showed many erythematous spots and individual round pustules. Diagnosis: psoriasis approaching the acute phase.

The drug was administered intravenously to the patient. After 10 days of treatment, the itching and weakness disappeared, the temperature dropped and the skin symptoms disappeared.

On day 20, the affected parts of the skin tissue had shrunk.

Individual pustules and papules on the flexor parts of the hands remained.

The acute symptoms of the disease returned after 4 months; this was a sign that the current treatment was inadequate.

A subsequent treatment cycle of 12 days made it possible to eliminate the main symptoms and led to a long-term remission of the main symptoms.

EXAMPLE 6A

Patient V., female, 42 years old, had been ill for 13 years, cured several times. However, in the last two years the traditional treatment remained without result. The patient complained about itching, general weakness. The examination revealed numerous patches of affected skin, many pustules, concentrations of erythematous spots.
Diagnosis: generalized psoriasis.

Administration of the drug for 10 days in a dose of 20 mg per kilogram of body weight led to the elimination of the itching and a lessening of the skin symptoms. Subsequent application to the skin of a solution of the drug in a 15% DMSO solution led quickly to the disappearance of the skin symptoms, including the pustules.

A tissue analysis of biopsy samples of residual skin formations revealed a considerable drop in the number of neutrophils in the epidermal cells.

After a 30-day treatment, the skin was completely clear; the remission period reached 8 months.

We claim:

1. A method for local treatment of skin irritation comprising topically applying an effective amount of a pharmaceutically acceptable salt of 5-amino-phthaloylhydrazide of the formula:

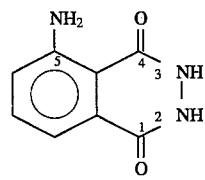

2. The method according to claim 1 wherein the pharmaceutically acceptable salt of 5-amino-phthaloylhydrazide is in a 20–30% solution of DMSO.

3. A method for treating infarct or of preventing rejection of transplants, comprising:

administering daily and intravenously 5-aminophthaloylhydrazide having the formula

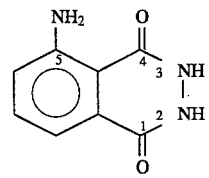

in a dose of 10 to 300 mg per kilogram of body weight and in the form of a pharmaceutically acceptable salt.

4. A method according to claim 1, wherein the pharmaceutically acceptable salt of 5-amino-phthaloylhydrazide is in a pharmaceutically acceptable carrier.

* * * * *